US009638708B2

(12) United States Patent
Wang et al.

(10) Patent No.: US 9,638,708 B2
(45) Date of Patent: May 2, 2017

(54) AUTOMATIC BIOCHEMICAL ANALYZER

(71) Applicant: Shenzhen Mindray Bio-Medical Electronics Co., Ltd., Shenzhen (CN)

(72) Inventors: Zhihong Wang, Shenzhen (CN); Qisong Liu, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days.

(21) Appl. No.: 14/517,644

(22) Filed: Oct. 17, 2014

(65) Prior Publication Data

US 2015/0037212 A1 Feb. 5, 2015

Related U.S. Application Data

(63) Continuation of application No. PCT/CN2013/074285, filed on Apr. 17, 2013.

(30) Foreign Application Priority Data

Apr. 17, 2012 (CN) .......................... 2012 1 0112960

(51) Int. Cl.
*G01N 35/02* (2006.01)
*G01N 35/04* (2006.01)

(52) U.S. Cl.
CPC ........... *G01N 35/025* (2013.01); *G01N 35/04* (2013.01); *G01N 2035/0444* (2013.01); *G01N 2035/0455* (2013.01)

(58) Field of Classification Search
CPC ............... G01N 2035/0444; G01N 2035/0445
See application file for complete search history.

(56) References Cited

U.S. PATENT DOCUMENTS

| 3,549,330 | A | * | 12/1970 | Jungner et al. ................. 422/64 |
| 3,764,268 | A | * | 10/1973 | Kosowsky ............. G01N 35/08 141/130 |
| 3,883,308 | A | * | 5/1975 | Matte ............................. 422/64 |
| 4,170,625 | A | * | 10/1979 | Welch ............................ 422/64 |

(Continued)

FOREIGN PATENT DOCUMENTS

| CN | 1963527 A | 5/2007 |
| CN | 101169450 A | 4/2008 |

(Continued)

*Primary Examiner* — Sean E Conley
*Assistant Examiner* — Benjamin Whatley
(74) *Attorney, Agent, or Firm* — Kory D. Christensen; Stoel Rives LLP

(57) ABSTRACT

An automatic biochemical analyzer is provided, the analyzer includes a reaction wheel that comprises an inner ring and outer ring, an interval of a photoelectric detection position of the inner ring and that of the outer ring is N cuvette positions along counterclockwise or clockwise direction, and an interval of a sample injecting position, a reagent injecting positions, a sample stirring position and a reagent stirring position of the inter ring and those of the outer ring respectively is M cuvette positions along the same direction, wherein M and N are integers and the difference between M and N is 0 or 1. The analyzer at the premise of ensuring the test flow, reducing wasting number of cuvettes, saving the cost of the whole analyzer, and the size of the reaction wheel will be as small as possible.

9 Claims, 4 Drawing Sheets

(56) References Cited

U.S. PATENT DOCUMENTS

| | | | |
|---|---|---|---|
| 5,104,808 A * | 4/1992 | Laska et al. .................... | 436/48 |
| 5,175,086 A * | 12/1992 | Takekawa ........ | G01N 33/54366 |
| | | | 422/63 |
| 5,183,638 A * | 2/1993 | Wakatake ....................... | 422/64 |
| 5,501,984 A * | 3/1996 | Hofstetter et al. ............ | 436/518 |
| 5,705,062 A * | 1/1998 | Knobel ........................ | 210/205 |
| 5,717,148 A * | 2/1998 | Ely .................... | G01N 35/1083 |
| | | | 422/63 |
| 6,691,748 B1 * | 2/2004 | Tajima .......................... | 141/130 |
| 2001/0019826 A1 * | 9/2001 | Ammann .......................... | 435/6 |
| 2002/0012916 A1 * | 1/2002 | Gundling et al. ................ | 435/6 |
| 2002/0064774 A1 * | 5/2002 | Schembri et al. ................ | 435/6 |
| 2003/0017084 A1 * | 1/2003 | Dale et al. .................... | 422/104 |
| 2003/0017613 A1 * | 1/2003 | Jakubowicz et al. .......... | 436/174 |
| 2003/0032191 A1 * | 2/2003 | Hilson et al. ................... | 436/47 |
| 2005/0123446 A1 * | 6/2005 | Yamazaki et al. .............. | 422/64 |
| 2005/0227360 A1 * | 10/2005 | Devlin ............................. | 436/45 |
| 2006/0062692 A1 * | 3/2006 | Tokieda et al. ................. | 422/64 |
| 2006/0204997 A1 * | 9/2006 | Macioszek et al. .............. | 435/6 |
| 2008/0102528 A1 * | 5/2008 | Xu et al. ......................... | 436/47 |
| 2008/0257390 A1 * | 10/2008 | Lee et al. ..................... | 134/56 R |
| 2009/0068748 A1 * | 3/2009 | Komatsu .......... | G01N 35/00584 |
| | | | 436/43 |
| 2009/0196793 A1 * | 8/2009 | Omuro et al. .................. | 422/64 |
| 2011/0236165 A1 * | 9/2011 | Kaiga ....................... | 414/222.07 |
| 2011/0256629 A1 * | 10/2011 | Wang et al. ..................... | 436/45 |
| 2012/0039748 A1 * | 2/2012 | Mimura et al. ................. | 422/63 |
| 2012/0322139 A1 * | 12/2012 | Nogami et al. ............ | 435/287.2 |

FOREIGN PATENT DOCUMENTS

| | | |
|---|---|---|
| CN | 102221626 A | 10/2011 |
| JP | 8-271517 A | 10/1996 |
| JP | 2010-145284 A | 7/2010 |

* cited by examiner

AUTOMATIC BIOCHEMICAL ANALYZER

TECHNICAL FILED

This disclosure relates to a biochemical analyzer.

SUMMARY

Disclosed herein are embodiments of a biochemical analyzer.

In one aspect, an automatic biochemical analyzer is provided that can include: a reaction wheel, which comprises an inner ring and an outer ring, wherein the reaction wheel is equally divided into multiple cuvette positions along a circumferential direction, the inner ring and the outer ring, respectively, having a photoelectric detection position, a sample injecting position, a reagent injecting position, a sample stirring position, a reagent stirring position and a cuvette cleaning position, and wherein these positions are located at a movement track of the reaction wheel; a photoelectric detection component, which is located at the photoelectric detection position of the inner ring and outer ring; a sample injecting component, which is located at the sample injecting position of the inner ring and outer ring; a reagent injecting component, which is located at the reagent injecting position of the inner ring and outer ring; a sample stirring component, which is located at the sample stirring position of the inner ring and outer ring; a reagent stirring component, which is located at the reagent stirring position of the inner ring and outer ring; and a cuvette cleaning component, which is located at the cuvette cleaning position of the inner ring and outer ring, and wherein the photoelectric detection position of the inner ring and the photoelectric detection position of the outer ring have a cuvette position interval of N along a counterclockwise or clockwise direction, and the sample injecting positions, the reagent injecting positions, the sample stirring positions and the reagent stirring positions of the inner ring and the outer ring, respectively, have a cuvette position interval of M along the same direction, M and N being natural numbers, and the difference between M and N being 0 or 1.

In one embodiment, the disclosed analyzer achieves a test flow, while reducing the number of the cuvettes wasted, reducing the cost of the whole analyzer, and minimizing the size of the reaction wheel. Various embodiments are convenient for controlling a high precision drive of the reaction wheel and reducing the size of the whole analyzer.

DETAILED DESCRIPTION

Figure 1:
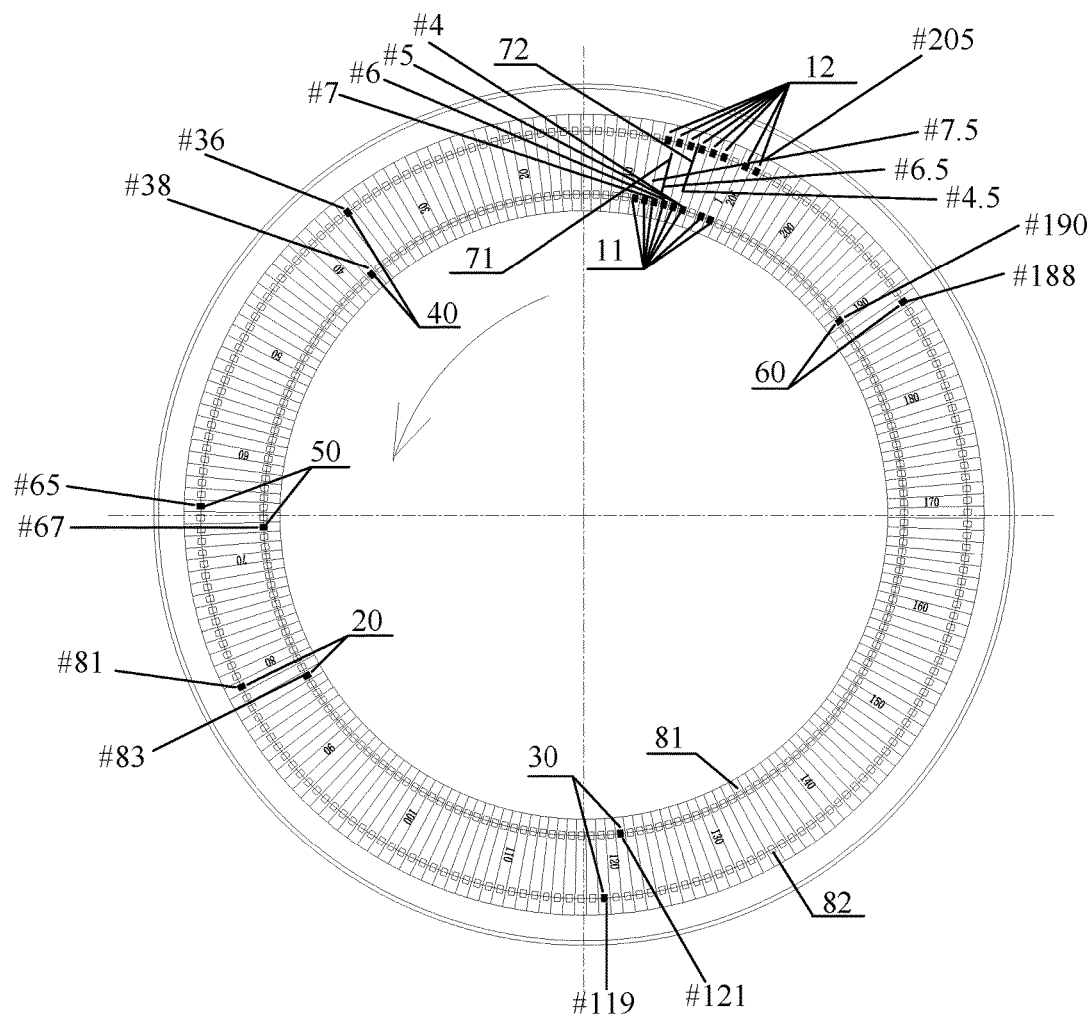
FIG. 1 shows a schematic diagram of an arrangement of work positions of the first embodiment.

For an automatic biochemical analyzer, in order to complete a series of test processes of sample injecting, reagent injecting, solution stirring, data acquisition, automatic cuvette cleaning, etc., a typical configuration requires a sample injecting component, a reagent injecting component, a stirring component, a photoelectric detection component, and a cuvette cleaning component. The relative position between a photoelectric detection position and a sample injecting position, a reagent injecting position, a sample stirring position, a reagent stirring position and a cuvette cleaning position on a reaction wheel directly effects test flow.

For a high speed automatic biochemical analyzer, two detection systems are integrated on one analyzer to obtain a higher test speed. Conventionally, a reaction wheel includes an inner ring and outer ring, in which case two detection systems corresponding to the inner ring cuvettes and outer ring cuvettes are used. The inner ring cuvettes are equally located along the circumferential direction; the outer ring cuvettes are equally located along the circumferential direction; the number of the cuvettes of the inner ring and the number of the cuvettes of the outer ring are the same and a one-to-one match; and an inner ring cuvette and a corresponding outer ring cuvette are set in the same radius of the reaction wheel. There are two photoelectric detection components for photoelectric detecting of the reaction solution of the inner ring and the outer ring. There are two sample injecting systems and two reagent injecting systems for injecting sample and reagent, and there are two stirring systems for stirring the reaction solution of the inner ring and the outer ring.

For an analyzer with a reaction wheel of a double ring and double detection system, a space occupied by a cuvette along the radius line of the inner ring and outer ring is defined as a cuvette position, the space occupied by cuvettes of the inner ring and outer ring along the same radius line is defined as the same cuvette position, and the photoelectric detection position of the inner ring and the outer ring requires at least one cuvette position interval according to space requirements of the photoelectric detection component (the interval of adjacent cuvettes is defined as a zero cuvette position).

Conventionally, the photoelectric detection positions of the inner ring and the outer ring have a cuvette position interval of one. However, for other work positions, including a sample injecting position, reagent injecting position, sample stirring position, reagent stirring position, etc., each work position of the inner ring and the outer ring is located at the same cuvette position, so the photoelectric detection positions of the inner ring and the outer ring have a cuvette interval of two more than the interval of each other work position of the inner ring and the outer ring. The photoelectric detection is performing while the reaction wheel is rotating, and each cuvette is rotated to the photoelectric detection position for detecting.

For a high speed automatic biochemical analyzer, the reaction wheel rotates or stops according to fixed rules. In a working cycle, the reaction wheel stops after rotating a predetermined number of cuvette positions along a fixed direction. During the reaction wheel rotation, the cuvette that rotates past the photoelectric detection position completes the photoelectric detecting. During the reaction wheel stop, sample injecting, reagent injecting, stirring, or cleaning the cuvette is completed according to test requirements. The reaction wheel rotates according to fixed rules repeatedly. The cuvette moves forward a certain number of cuvette positions along the circumferential direction of the reaction wheel after a predetermined cycle, so that each cuvette is tested in turn according to the same flow, which includes reagent injecting, sample injecting, reaction solution stirring, cuvette cleaning, etc.

Typically, the photoelectric detection positions of the inner ring and the outer ring have a cuvette position interval of one, and each other work position of the inner ring and the outer ring is located at the same cuvette position, because there is a cuvette position interval between the photoelectric detection position of the inner ring and the outer ring. Photoelectric detection of the inner or outer cuvette is performed in different working cycles; that is, photoelectric detection of a cuvette of an inner ring starts later than that of a cuvette of an outer ring in certain cycles. At the same time, a cuvette of a ring completes photoelectric detection later than the cuvette of an outer ring of the same cycle, but other steps of the test flow of the inner ring and the outer ring are performed at the same time. Time is generally required between photoelectric detection, reagent injecting, sample injecting, and stirring, so as to ensure time consistency of the inner and outer photoelectric detection. In fact, to ensure test flow consistency, the number of photoelectric detections of the inner ring and the number of photoelectric detections of the outer ring must be the same. Extra photoelectric detection data have to be given up. The number and time of photoelectric detections will directly affect the number of configurations of the cuvettes. Conventional systems will lead to waste of at least four cuvette positions, and at least eight more cuvette positions need to be configured to ensure the test flow, leading to wasting a number of the cuvettes. The number of the cuvettes will affect the cost of the analyzer, and the size of the reaction wheel will be affected also. The greater the number of cuvettes, the bigger the size of the reaction wheel. Furthermore, greater challenges come from high precision drive control of the bigger reaction wheel, and the size of the whole analyzer will be increased.

Referring now to the figures, FIG. 1 shows an arrangement of work positions of a first embodiment. There are 206 inner cuvettes 81 in the inner ring of the reaction wheel along the circumferential direction, and there are 206 outer cuvettes 82 in the outer ring of the reaction wheel along the circumferential direction. Accordingly, the inner ring and the outer ring of the reaction wheel are numbered by position coordinate, and the inner ring and the outer ring of the reaction wheel are numbered uniformly. In one embodiment, the numbering starts from the eighth step cleaning position of the reaction wheel of the inner ring, which position coordinate is defined as #1. The position coordinates are fixed and increase along the counterclockwise direction, so the position coordinate of the first step cleaning position of the reaction wheel of the inner ring is defined as #9. Accordingly, the position coordinate of the eighth step cleaning position of the reaction wheel of the outer ring is #205, and the position coordinate of the first step cleaning position of the reaction wheel of the outer ring is #7. The cuvettes are also numbered. The number of inner and outer cuvettes is the same, and the cuvettes are numbered #1-#206 along the counterclockwise direction.

The photoelectric detection positions of the inner ring and the outer ring have a cuvette position interval of at least one for arrangement requirements. In one embodiment, the photoelectric detection positions of the inner ring and the outer ring have a cuvette position interval of one. As shown in FIG. 1, the photoelectric detection position of the reaction wheel of the inner ring 71 is located at #6.5 (between #6 and #7), and the photoelectric detection position of the reaction wheel of the outer ring 72 is located at #4.5 (between #4 and #5).

To ensure test flow consistency, the cleaning position 11 of the reaction wheel of the inner ring and the cleaning position 12 of the reaction wheel of the outer ring have a cuvette position interval of one along the same direction (counterclockwise or clockwise); that is, the cleaning positions of the reaction wheel of the inner ring are located at #1-#9, wherein the first step cleaning position of the reaction wheel of the inner ring is located at #9 and the eighth step cleaning position of the reaction wheel of the inner ring is located at #1; and the cleaning positions of the reaction wheel of the outer ring are located at #205-#7, wherein the first step cleaning position of the reaction wheel of the outer ring is located at #7 and the eighth step cleaning position of the reaction wheel of the outer ring is located at #205.

The first reagent injecting position 20, the sample injecting position 30, the sample stirring position 40, the second reagent injecting position 50, and the reagent stirring position 60 of the inner ring and the outer ring, respectively, have a cuvette position interval of one also; that is, the first reagent injecting position of the reaction wheel of the inner ring is located at #83, the first reagent injecting position of the reaction wheel of the outer ring is located at #81, the sample injecting position of the reaction wheel of the inner ring is located at #121, the sample injecting position of the reaction wheel of the outer ring is located at #119, the sample stirring position of the reaction wheel of the inner ring is located at #38, the sample stirring position of the reaction wheel of the outer ring is located at #36, the second reagent injecting position of the inner ring is located at #67, the second reagent injecting position of the reaction wheel of the outer ring is located at #65, the reagent stirring position of the reaction wheel of the inner ring is located at #190, and the reagent stirring position of the reaction wheel of the outer ring is located at #188.

Figure 2:
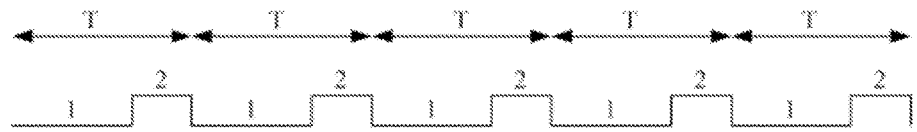
FIG. 2 shows a timing diagram of cycle actions occurring on the reaction wheel.

FIG. 2 is a timing diagram of cycle actions occurring on the reaction wheel. "1" represents a stopping period of the reaction wheel, and "2" represents a rotation period of the reaction wheel. In one embodiment, the reaction wheel rotates in a counterclockwise direction, and 41 cuvette positions are passed during the rotation period, so 205 cuvette positions are passed in every five cycles, and then the cuvette moves forward one cuvette position in the clockwise direction. In every stop period of a cycle of the reaction wheel, the first reagent injecting component injects the first reagent into a cuvette of the reaction wheel of the inner ring and the outer ring located at the first reagent injecting position respectively according to requirements.

The sample injecting component injects sample into the cuvette of the reaction wheel of the inner ring and the outer ring located at the sample injecting position respectively according to requirements. The sample stirring component stirs the solution of the cuvettes of the inner ring and the outer ring located at the sample stirring position respectively according to requirements. The second reagent injecting component injects the second reagent into the cuvettes of the reaction wheel of the inner ring and the outer ring located at the second reagent injecting position respectively according to requirements. The reagent stirring component stirs the solution of the cuvettes of the inner ring and the outer ring located at the reagent stirring position respectively according to requirements.

In various embodiments, there are acceleration and deceleration processes in the rotation period of every cycle, and an unsteady rotation speed of the passing photoelectric detection position will cause photoelectric data to be unreliable. The photoelectric detection components of the reaction wheel of the inner ring and the outer ring simply gather data that correspond to cuvettes passing photoelectric detection positions with uniform velocity. The photoelectric data corresponding to acceleration and deceleration processes of the reaction wheel are not gathered. In one embodiment, the reaction wheel passes 3.5 cuvette positions during the acceleration process, the reaction wheel passes 2.5 cuvette positions during the deceleration process, and the reaction wheel passes 35 cuvette positions with even speed between the acceleration and deceleration processes.

The following is a test flow based on one arrangement of work positions in the reaction wheel and action cycle, wherein each stopping period 1 and rotation period 2 of the reaction wheel is defined as a cycle T. The first cycle is defined as beginning when the #1 cuvette of the reaction wheel of the inner ring and the #205 cuvette of the reaction wheel of the outer ring are stopped at the cleaning position. The test flow is described as follows.

In the first cycle, the #1 cuvette of the reaction wheel of the inner ring and the #205 cuvette of the reaction wheel of the outer ring are simultaneously stopped at the first step cleaning position of the reaction wheel of the inner ring and the outer ring, respectively, performing the first step cleaning of the #1 cuvette of the reaction wheel of the inner ring and the #205 cuvette of the reaction wheel of the outer ring.

In the sixth cycle, the #1 cuvette of the reaction wheel of the inner ring and the #205 cuvette of the reaction wheel of the outer ring are simultaneously stopped at the second step cleaning position of the reaction wheel of the inner ring and the outer ring, respectively, performing the second step cleaning of the #1 cuvette of the reaction wheel of the inner ring and the #205 cuvette of the reaction wheel of the outer ring.

In the 11th cycle, the #1 cuvette of the reaction wheel of the inner ring and the #205 cuvette of the reaction wheel of the outer ring are simultaneously stopped at the third step cleaning position of the reaction wheel of the inner ring and the outer ring, respectively, performing the third step cleaning of the #1 cuvette of the reaction wheel of the inner ring and the #205 cuvette of the reaction wheel of the outer ring.

In the 16th cycle, the #1 cuvette of the reaction wheel of the inner ring and the #205 cuvette of the reaction wheel of the outer ring are simultaneously stopped at the fourth step cleaning position of the reaction wheel of the inner ring and the outer ring, respectively, performing the fourth step cleaning of the #1 cuvette of the reaction wheel of the inner ring and the #205 cuvette of the reaction wheel of the outer ring.

In the 21st cycle, the #1 cuvette of the reaction wheel of the inner ring and the #205 cuvette of the reaction wheel of the outer ring are simultaneously stopped at the fifth step cleaning position of the reaction wheel of the inner ring and the outer ring, respectively, performing the fifth step cleaning of the #1 cuvette of the reaction wheel of the inner ring and the #205 cuvette of the reaction wheel of the outer ring.

In the 26th cycle, the #1 cuvette of the reaction wheel of the inner ring and the #205 cuvette of the reaction wheel of the outer ring are simultaneously stopped at the sixth step cleaning position of the reaction wheel of the inner ring and the outer ring, respectively, performing the sixth step cleaning of the #1 cuvette of the reaction wheel of the inner ring and the #205 cuvette of the reaction wheel of the outer ring. While the reaction wheel is rotating, after the speed of the reaction wheel is even, the #1 cuvette of the reaction wheel of the inner ring and the #205 cuvette of the reaction wheel of the outer ring arrive at the photoelectric detection position, where photoelectric data gathering of the blank cuvettes is performed for the first time.

In the 31st cycle, the #1 cuvette of the reaction wheel of the inner ring and the #205 cuvette of the reaction wheel of the outer ring are simultaneously stopped at a cuvette position between the sixth step cleaning position and the seventh step cleaning position of the reaction wheel of the inner ring and the outer ring, respectively. While the reaction wheel is rotating, after the speed of the reaction wheel is even, the #1 cuvette of the reaction wheel of the inner ring and the #205 cuvette of the reaction wheel of the outer ring arrive at the photoelectric detection position, where photoelectric data gathering of the blank cuvettes is performed for the second time.

In the 36th cycle, the #1 cuvette of the reaction wheel of the inner ring and the #205 cuvette of the reaction wheel of the outer ring are simultaneously stopped at the seventh step cleaning position of the reaction wheel of the inner ring and the outer ring, respectively, performing the seventh step cleaning of the #1 cuvette of the reaction wheel of the inner ring and the #205 cuvette of the reaction wheel of the outer ring.

In the 41st cycle, the #1 cuvette of the reaction wheel of the inner ring and the #205 cuvette of the reaction wheel of the outer ring are simultaneously stopped at the eighth step cleaning position of the reaction wheel of the inner ring and the outer ring, respectively, performing the eighth step cleaning of the #1 cuvette of the reaction wheel of the inner ring and the #205 cuvette of the reaction wheel of the outer ring.

In 43rd cycle, inner cuvette #1 and outer cuvette #205 are simultaneously stopped at the first reagent dispensing position of the reaction wheel of the inner ring and the outer ring, respectively, and two reagent probes add the first reagent to the inner cuvette #1 and the outer cuvette #205, respectively.

In 46th cycle, the #1 cuvette of the reaction wheel of the inner ring and the #205 cuvette of the reaction wheel of the outer ring pass the photoelectric detection position with even speed, while the reaction wheel is rotating, and photoelectric detection gathering after injecting reagent is performed for the first time. The #1 cuvette of the reaction wheel of the inner ring and the #205 cuvette of the reaction wheel of the outer ring will pass the photoelectric detection position with even speed once every five cycles afterwards, at which points the photoelectric detection gathering will be performed.

In the 59th cycle, the #1 cuvette of the reaction wheel of the inner ring and the #205 cuvette of the reaction wheel of the outer ring are simultaneously stopped at the sample injecting position of the reaction wheel of the inner ring and the outer ring, respectively, and two sample probes inject the sample into the #1 cuvette of the reaction wheel of the inner ring and the #205 cuvette of the reaction wheel of the outer ring, respectively.

In the 62nd cycle, the #1 cuvette of the reaction wheel of the inner ring and the #205 cuvette of the reaction wheel of the outer ring are simultaneously stopped at the sample stirring position of the reaction wheel of the inner ring and the outer ring, respectively. The sample stirring component stirs the solution of the #1 cuvette of the reaction wheel of the inner ring and the #205 cuvette of the reaction wheel of the outer ring, respectively.

In the 123rd cycle, the #1 cuvette of the reaction wheel of the inner ring and the #205 cuvette of the reaction wheel of the outer ring are simultaneously stopped at the second reagent position of the reaction wheel of the inner ring and the outer ring, respectively. Two reagent probes inject the second reagent into the #1 cuvette of the reaction wheel of the inner ring and the #205 cuvette of the reaction wheel of the outer ring, respectively, according to test requirements. Injecting a second reagent is necessary for a double reagent item, but not for a signal reagent item in one embodiment.

In the 126th cycle, the #1 cuvette of the reaction wheel of the inner ring and the #205 cuvette of the reaction wheel of the outer ring are simultaneously stopped at the reagent stirring position of the reaction wheel of the inner ring and the outer ring, respectively. The reagent stirring component stirs the solution of the #1 cuvette of the reaction wheel of the inner ring and the #205 cuvette of the reaction wheel of the outer ring, respectively.

In the 206th cycle, the #1 cuvette of the reaction wheel of the inner ring and the #205 cuvette of the reaction wheel of the outer ring are simultaneously stopped at the #175 cuvette position of the reaction wheel of the inner ring and the #173 cuvette position of the reaction wheel of the outer ring, respectively.

While the reaction wheel is rotating, the #1 cuvette of the reaction wheel of the inner ring and the #205 cuvette of the reaction wheel of the outer ring pass the photoelectric detection position for the last time before the cuvette cleaning. Photoelectric data gathering for the 33rd time after injecting the first reagent is performed, after which the test is complete.

In the 207th cycle, the #1 cuvette of the reaction wheel of the inner ring and the #205 cuvette of the reaction wheel of the outer ring are simultaneously stopped at the first step cleaning position of the reaction wheel of the inner ring and the outer ring, respectively, performing the first step cleaning of the #1 cuvette of the reaction wheel of the inner ring and the #205 cuvette of the reaction wheel of the outer ring.

The cuvette can be used for the next test after eight cleaning steps are finished, and each cuvette of the reaction wheel of the inner ring and the outer ring is repeatedly used for testing according to the flow above.

Figure 3:
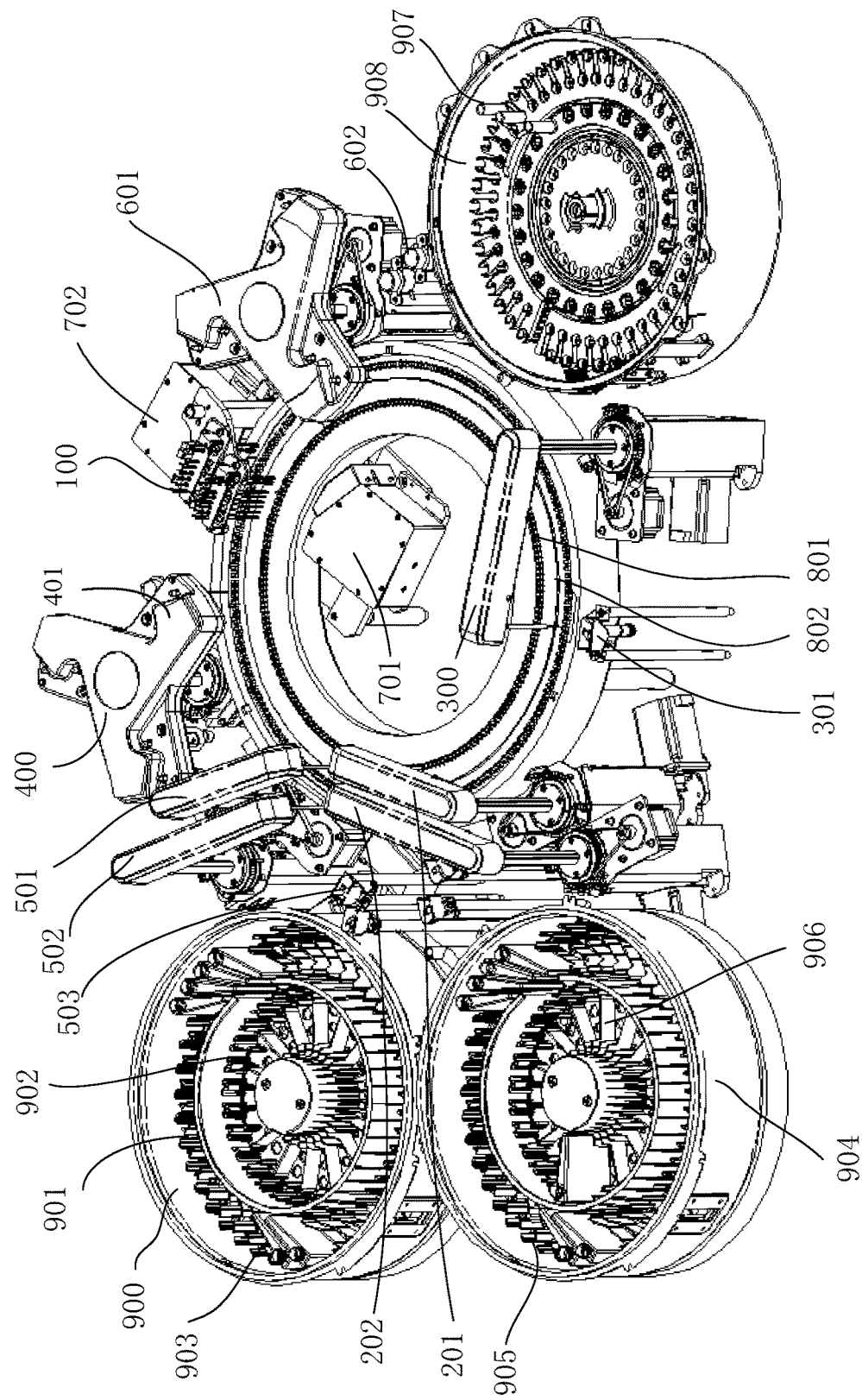
FIG. 3 shows a schematic diagram of a biochemical analyzer arrangement.

FIG. 3 shows an embodiment of a biochemical analyzer arrangement. The first reagent probe R11 (201) performs reagent drawing from a reagent drawing position of the first reagent wheel of the outer ring 905, injecting the first reagent into the first reagent injecting position of the reaction wheel of the inner ring 801, cleaning itself at the wash tank in sequence every cycle. The first reagent probe R12 (202) performs reagent drawing from the reagent drawing position of the first reagent wheel of the inner ring 906, injecting the first reagent into the first reagent injecting position of the reaction wheel of the outer ring 802, cleaning itself at the wash tank every cycle in sequence. The reagent probes R11 and R12 are rotated to the first reagent wheel for drawing the first reagent along the same direction, and similarly, the reagent probes R11 and R12 are also rotated to the reaction wheel for injecting the first reagent along the same direction. If just one reagent probe is needed to draw and inject the reagent in a cycle, the other probe rotates with it to ensure the one probe is moving normally.

There are two sample probes fixed to the sample dispensing component 300. The sample injecting component performs sample drawing from the sample drawing position of a sample wheel 908, and then injects the sample into the cuvette of the reaction wheel of the inner ring and the outer ring, cleaning itself at the cleaning tank 301 in sequence every cycle.

Sample stirring module 400 consist of three group of stirring rod assemblies 401, each group of stirring rod assembly has two stirring rods, and stirrers reaction solution in cuvettes which are located at sample stirring position of inner and outer ring respectively. While one group of stirring rod assembly is stirring, the other two groups of stirring rod assemblies are performing the 1st step cleaning and the 2nd step cleaning. These three groups of stirring rod assemblies perform the 1st step cleaning, the 2nd step cleaning, stirring and cleaning in turn, one group of stirring rod assembly is used for stirring once every three cycles.

The second reagent probe R21 (501) performs drawing of the second reagent from the reagent drawing position of the second reagent wheel of the outer ring 901, injecting the second reagent to the second reagent injecting position of the reaction wheel of the inner ring 801, cleaning itself at the wash tank in sequence every cycle. The second reagent probe R22 (502) performs drawing of the second reagent from the reagent drawing position of the second reagent wheel of the inner ring 902, injecting the reagent into the first reagent injecting position of the reaction wheel of the outer ring 802 in sequence every cycle. The reagent probes R21 and R22 are rotated to the second reagent wheel along the same direction, and similarly, the reagent probes R21 and R22 are rotated to the reaction wheel along the same direction. If only one reagent probe needs to draw and inject the reagent in a cycle, the other probe rotates with it to ensure the one probe is moving normally.

The reagent stirring component 601 may include three groups of stirring rod assemblies, each group having two stirring rods, and stirrers reaction solution in cuvettes that are located at the reagent stirring position of the reaction wheel of the inner ring and the outer ring, respectively. While one group of stirring rod assembly is stirring, the other two groups of stirring rod assemblies are performing the first step cleaning and the second step cleaning. These three groups of stirring rod assemblies perform the first step cleaning, the second step cleaning, stirring, and cleaning in turn, with one group of stirring rod assembly being used for stirring once every three cycles.

A cuvette cleaning component 100 cleans cuvettes of the reaction wheel of the inner ring and the outer ring when they are stopped at the cuvette cleaning position of the reaction wheel during each cycle.

The photoelectric detection component 701 of the reaction wheel of the inner ring and photoelectric detection component 702 of the reaction wheel of the outer ring perform photoelectric data gathering of the cuvettes, which pass the photoelectric detection components with even speed in each cycle.

The first reagent wheel 904 and the second reagent wheel 900 place multiple reagent bottles 903, which contain the reagents required by the test. The sample wheel places multiple sample containers 907, which contain the samples required by test.

The stirring rods of the sample stirring component and the reagent stirring component are the same in one embodiment, and a wash tank for cleaning the stirring rods of the sample and reagent may be the same also. FIG. 3 only shows one stirring rod and a wash tank 602. Each wash tank is located under the cleaning portion of the stirring component. FIG. 3 only shows a wash tank 503 of the second reagent probe R21, and wash tanks of the other three reagent probes are not shown. The reagent probes, the sample probes, and the stirring rod perform predetermined actions according to their fixed movement track respectively. The reagent drawing position, cleaning position, and reagent injecting position are set in the fixed movement track of the reagent probe. The sample drawing position, cleaning position, and sample injecting position are set in the fixed movement track of the sample probe.

The sample wheel, the first reagent wheel of the inner ring, the first reagent wheel of the outer ring, the second reagent wheel of the inner ring, and the second reagent wheel of the outer ring perform stopping actions and rotation actions in each cycle. In stopping periods, the probes draw liquid (reagent or sample) from the wheels. In the rotation periods, the wheels are rotated to the liquid drawing position for the next cycle. The reaction wheel performs predetermined stop and rotation actions, and rotates cuvette positions of a fixed number along the counterclockwise direction in every cycle. The reaction wheel rotates 41 cuvette positions in one embodiment.

In another embodiment, instead of sample injecting positions, reagent injecting positions, sample stirring positions, and reagent stirring positions are not located at the same cuvette position. The sample injecting position, reagent injecting position, sample stirring position and reagent stirring position respectively have a cuvette position interval of the same number as the number of photoelectric detection positions along the same direction (counterclockwise or clockwise). The cleaning position does not have a cuvette position interval equal to the photoelectric detection position's. Accordingly, there is a difference in direction, cuvette position interval, or both. So there is only difference in the maximum reaction time. The maximum reaction time is defined as starting when the first reagent is injected and ending when photoelectric detection for the last time is completed, wherein photoelectric detection for the last time is defined as photoelectric data gathering for the last time when a cuvette is rotated with even speed before the first step cuvette cleaning. If the cuvette could also be rotated for photoelectric detection with even speed after the first step cleaning and before the next test, but the photoelectric detection is invalid because the cuvette has been cleaned. If the cuvette cleaning position is a bottleneck of the maximum reaction time, the maximum reaction time will be different, but it is acceptable if the reaction time of the photoelectric detection system is shorter than test requirements. If the photoelectric detection position instead of the cuvette cleaning position is a bottleneck of the maximum reaction time, the maximum reaction time will not be affected if the cleaning position of the reaction wheel of the inner ring and the outer ring does not have a cuvette position interval of the same number as that of the photoelectric detection position. For the former situation, it will reduce almost a half number of increased cuvettes caused by difference of the cuvette position interval between photoelectric detection position and the other work positions. For the latter situation, the number of the cuvettes could not be increased because of the difference of the cuvette position interval between the photoelectric detection position and other work positions.

In another embodiment, the photoelectric detection position of the inner ring and the photoelectric detection position of the outer ring have a cuvette position interval of N. The sample injecting positions, the reagent injecting positions, the sample stirring positions, and the reagent stirring positions of the inner ring and the outer ring, respectively, have a cuvette position interval of M along the same direction, M and N being natural numbers, and M≠N, e.g., M−N=1, or N−M=1. Although it is not optimal, this could reduce wasting cuvettes.

The analyzer can be realized by a computer or related hardware. All procedures may be stored in a computer readable storage medium and executed by a processor. Storage media could be a disk, CD, Read-Only Memory (ROM) or Random Access Memory (RAM), etc.

Figure 4:
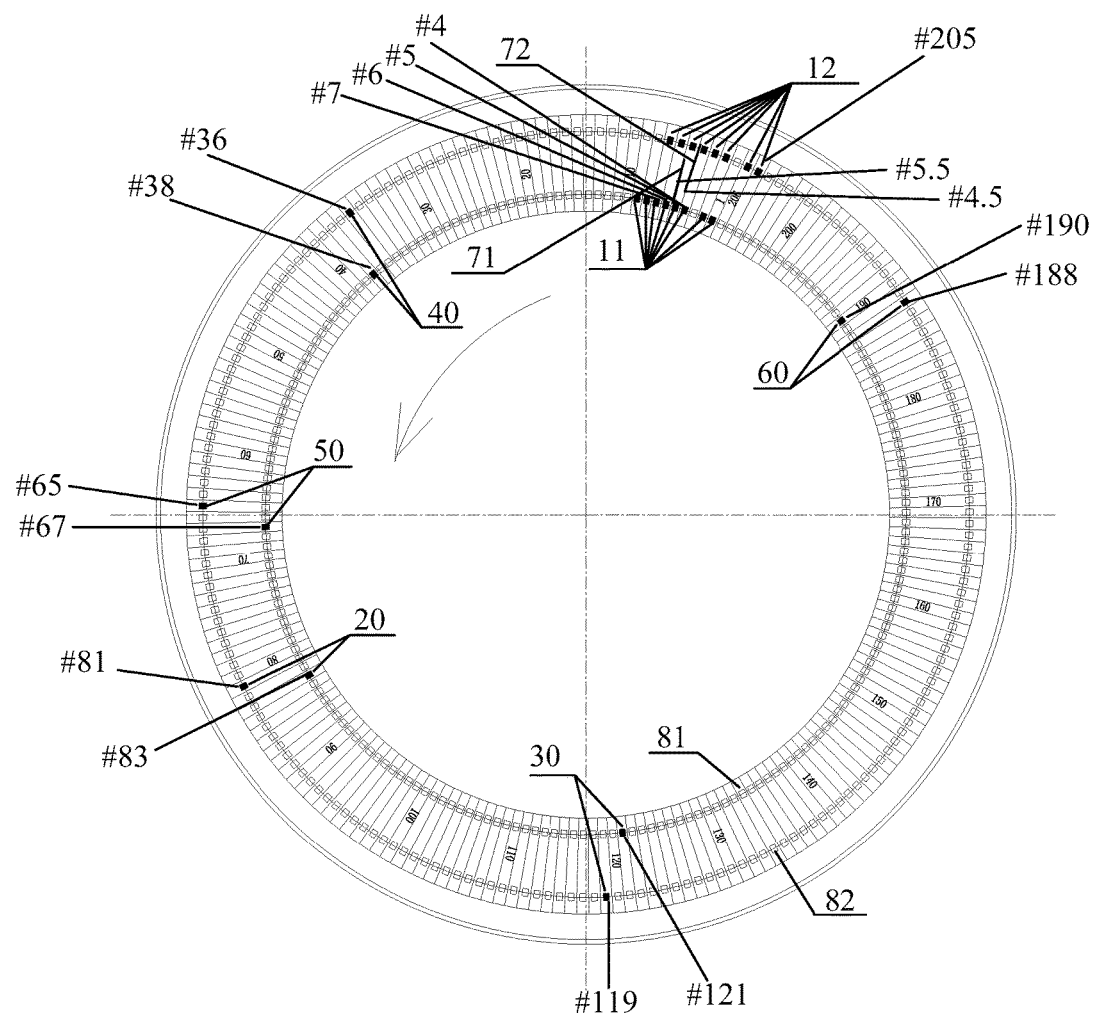
FIG. 4 shows a schematic diagram of an arrangement of work positions according to another embodiment.
Figure 5:
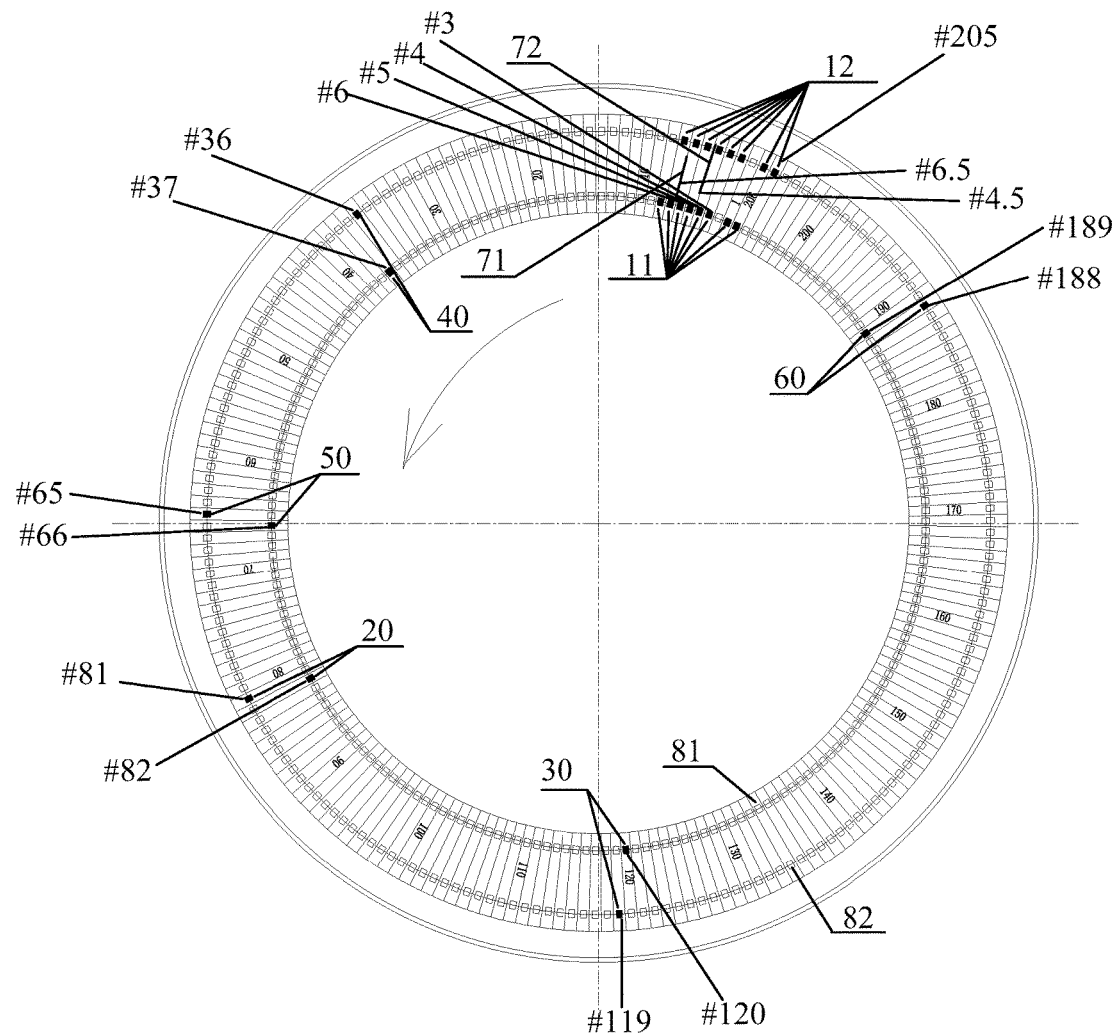
FIG. 5 shows a schematic diagram of an arrangement of work positions according to another embodiment.

Various configurations of the analyzer are disclosed herein. For example, FIG. 1 depicts a reaction wheel wherein the photoelectric detection position of the inner ring (located at #6.5) is offset relative to that of the outer ring (located at #4.5) by an interval of N =1 cuvette positions, and the sample injecting position, the reagent injecting position, the sample stirring position, and the reagent stirring position of the inner ring are respectively offset relative to those of the outer ring by an interval of M =1 cuvette positions, and the difference between M and N is 0. FIG. 4 depicts a reaction wheel wherein the photoelectric detection position of the inner ring (located at #5.5) is offset relative to that of the outer ring (located at #4.5) by an interval of N =0 cuvette positions, and the sample injecting position, the reagent injecting position, the sample stirring position, and the reagent stirring position of the inner ring are respectively offset relative to those of the outer ring by an interval of M =1 cuvette positions, and the difference between M and N is 1. FIG. 5 depicts a reaction wheel wherein the photoelectric detection position of the inner ring is offset relative to that of the outer ring by an interval of N =1 cuvette positions, and the sample injecting position, the reagent injecting position, the sample stirring position, and the reagent stirring position of the inner ring are respectively offset relative to those of the outer ring by an interval of M =0 cuvette positions, and the difference between M and N is 1. As shown in FIGS. 1, 4, and 5, the zero cuvette position is defined as an interval of adjacent cuvettes, such that when N is 0, the photoelectric detection position of the inner ring is offset relative to that of the outer ring by an interval of one cuvette position, and when N is 1, the photoelectric detection position of the inner ring is offset relative to that of the outer ring by an interval of two cuvette positions. Similarly, when M is 0, the sample injecting position, the reagent injecting position, the sample stirring position, and the reagent stirring position of the inner ring are respectively offset relative to those of the outer ring by an interval of one cuvette position, and when M is 1, the sample injecting position, the reagent injecting position, the sample stirring position, and the reagent stirring position of the inner ring are respectively offset relative to those of the outer ring by an interval of two cuvette positions.

Those having skill in the art will appreciate that many changes may be made to the details of the above-described embodiments without departing from the underlying principles of the invention. The scope of the present invention should, therefore, be determined only by the following claims.

What is claimed is:

1. An automatic biochemical analyzer, comprising:
   a reaction wheel that comprises an inner ring and an outer ring, and the inner ring and the outer ring are equally divided into multiple cuvette positions respectively along a circumferential direction of the reaction wheel, a photoelectric detection position, a sample injecting position, a reagent injecting position, a sample stirring position, a reagent stirring position, and a cuvette cleaning position of the inner ring and those of the outer ring respectively are located at a movement track of a cuvette in the reaction wheel;
   a photoelectric detection component that is configured to operate at the photoelectric detection position of the inner ring and that of the outer ring;
   a sample injecting component that is configured to operate at the sample injecting position of the inner ring and that of the outer ring;
   a reagent injecting component that is configured to operate at the reagent injecting position of the inner ring and that of the outer ring;
   a sample stirring component that is configured to operate at the sample stirring position of the inner ring and that of the outer ring;

a reagent stirring component that is configured to operate at the reagent stirring position of the inner ring and that of the outer ring; and a cuvette cleaning component that is configured to operate at the cuvette cleaning position of the inner ring and that of the outer ring, wherein the photoelectric detection position of the inner ring is offset relative to that of the outer ring by an interval of N cuvette positions along a counterclockwise or clockwise direction, and the sample injecting position, the reagent injecting position, the sample stirring position, and the reagent stirring position of the inner ring are respectively offset relative to those of the outer ring by an interval of M cuvette positions along the same direction, wherein M and N are each either 0 or 1, and the difference between M and N is 0 or 1, wherein when N is 0, the photoelectric detection position of the inner ring is offset relative to that of the outer ring by an interval of one cuvette position, and wherein when N is 1, the photoelectric detection position of the inner ring is offset relative to that of the outer ring by an interval of two cuvette positions, and wherein when M is 0, the sample injecting position, the reagent injecting position, the sample stirring position, and the reagent stirring position of the inner ring are respectively offset relative to those of the outer ring by an interval of one cuvette position, and wherein when M is 1, the sample injecting position, the reagent injecting position, the sample stirring position, and the reagent stirring position of the inner ring are respectively offset relative to those of the outer ring by an interval of two cuvette positions.

2. The analyzer of claim 1, wherein the difference between M and N is 0.

3. The analyzer of claim 1, wherein an interval between the cuvette cleaning position of the inner ring and that of the outer ring is M cuvette positions along the same direction.

4. The analyzer of claim 2, wherein an interval between the cuvette cleaning position of the inner ring and that of the outer ring is M cuvette positions along the same direction.

5. The analyzer of claim 3, wherein the difference between M and N is 1.

6. The analyzer of claim 1, wherein the reagent injecting position of the inner ring and that of the outer ring respectively further comprises a first reagent injecting position and a second reagent injecting position on both the inner and the outer rings, the reagent injecting component of the inner ring further comprises a first reagent probe for dispensing a first reagent at the first reagent injecting position on the inner ring and a second reagent probe for dispensing a second reagent at the second reagent injecting position on the inner ring, and the reagent injecting component of the outer ring further comprises a third reagent probe for dispensing the first reagent at the first reagent injecting position on the outer ring and a fourth reagent probe for dispensing the second reagent at the second reagent injecting position on the outer ring.

7. The analyzer of claim 6, wherein the analyzer further comprises a first reagent wheel and a second reagent wheel which are located at a side of the reaction wheel and configured to place a first reagent and a second reagent respectively.

8. The analyzer of claim 6, wherein the cuvette cleaning component cleans cuvettes located at the cuvette cleaning position of the inner ring and the cuvette cleaning position of the outer ring simultaneously.

9. The analyzer of claim 6, wherein the reagent injecting position of the inner ring and that of the outer ring respectively further comprises a first wash tank for cleaning the first reagent probe, a second wash tank for cleaning the second reagent probe, a third wash tank for cleaning the third reagent probe, and a fourth wash tank for cleaning the fourth reagent probe.

* * * * *